(12) United States Patent
Devarakonda et al.

(10) Patent No.: US 10,133,847 B2
(45) Date of Patent: Nov. 20, 2018

(54) AUTOMATED MEDICAL PROBLEM LIST GENERATION FROM ELECTRONIC MEDICAL RECORD

(71) Applicant: International Business Machines Corporation, Armonk, NY (US)

(72) Inventors: Murthy V. Devarakonda, Peekskill, NY (US); Ching-Huei Tsou, Briarcliff Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 301 days.

(21) Appl. No.: 14/300,699

(22) Filed: Jun. 10, 2014

(65) Prior Publication Data

US 2015/0356270 A1    Dec. 10, 2015

(51) Int. Cl.
*G06F 19/00* (2018.01)
*G16H 15/00* (2018.01)
*G16H 10/60* (2018.01)
*G16H 50/70* (2018.01)

(52) U.S. Cl.
CPC ......... *G06F 19/3443* (2013.01); *G16H 10/60* (2018.01); *G16H 15/00* (2018.01); *G16H 50/70* (2018.01)

(58) Field of Classification Search
CPC ............... G06F 19/3443; G06F 19/322; G06F 19/3418; G06F 19/30; G06F 19/325; G16H 15/00; G16H 10/60; G16H 50/30; G06Q 50/24; G06Q 10/06393
See application file for complete search history.

(56) References Cited

U.S. PATENT DOCUMENTS

| | | | |
|---|---|---|---|
| 7,958,067 B2* | 6/2011 | Schmidtler | G06Q 10/10 706/12 |
| 8,856,156 B1 | 10/2014 | McNair et al. | |
| 9,690,861 B2 | 6/2017 | Boloor et al. | |
| 2008/0201280 A1* | 8/2008 | Martin | G06Q 50/24 706/12 |
| 2008/0294459 A1* | 11/2008 | Angell | G06F 19/328 705/2 |

(Continued)

OTHER PUBLICATIONS

Stephane M. Meystre et al., "Randomized controlled trial of an automated problem list with improved sensitivity", International journal of medical informatics 7 7 ( 2 0 0 8 ) 602-612.

(Continued)

*Primary Examiner* — Maroun P Kanaan
(74) *Attorney, Agent, or Firm* — Gibb & Riley, LLC

(57) ABSTRACT

Methods, systems, and devices map data of an electronic medical record to standardized medical concepts. The standardized medical concepts are defined by medical industry standards organizations. The methods, systems, and devices identify medical problem concepts, from the standardized medical concepts, generate feature values of the medical problem concepts based on features within the mapped standardized medical concepts, and weight the medical problem concepts based on the feature values according to a weighting function. These methods, systems, and devices identify medical problems as ones of the medical problem concepts that have a weighted score above a threshold, according to the weighting, and output a list of the medical problems.

17 Claims, 6 Drawing Sheets

(56) References Cited

U.S. PATENT DOCUMENTS

| | | | |
|---|---|---|---|
| 2009/0292557 A1* | 11/2009 | Sirohey | G06F 19/3443 |
| | | | 705/3 |
| 2010/0281025 A1* | 11/2010 | Tsatsou | G06F 17/30699 |
| | | | 707/733 |
| 2011/0208822 A1 | 8/2011 | Rathod | |
| 2013/0132308 A1 | 5/2013 | Boss et al. | |
| 2013/0218596 A1 | 8/2013 | Gome et al. | |
| 2015/0294088 A1 | 10/2015 | Walker et al. | |

OTHER PUBLICATIONS

Stephane M. Meystre et al., "Natural language processing to extract medical problems from electronic clinical documents: Performance evaluation", Journal of Biomedical Informatics 39 (2006) 589-599.

Stephane Meystre et al., "Automation of a problem list using natural language processing", BMC Medical Informatics & Decision Making Apr. 22, 2014. pp. 1-11.

Lise Poissant et al., "Assessing the accuracy of an inter-institutional automated patient-specific health problem list", BMC Medical Informatics and Decision Making 2010, 10:10 http://www.biomedcentral.com, 2010, pp. 1-10.

U.S. Appl. No. 14/309,058, Office Action Communication dated Jul. 27, 2017, pp. 1-26.

U.S. Appl. No. 14/309,058, Office Action Communication dated Apr. 20, 2018, pp. 1-14.

U.S. Appl. No. 14/309,058, Office Action Communication dated Jan. 4, 2018, pp. 1-25.

* cited by examiner

AUTOMATED MEDICAL PROBLEM LIST GENERATION FROM ELECTRONIC MEDICAL RECORD

BACKGROUND

The present disclosure relates to electronic medical records and more particularly, to methods, systems, and devices for automatically generating a list of medical problems from such electronic medical records.

Patient records are commonly maintained within computerized systems as electronic medical records (EMR). Such patient records are typically large, 50-300 Mbytes of data, with several hundreds of clinical notes, and can include many structured data tables each with dozens of entries. Because of their size and complexity, electronic medical records can be challenging for a human to read, and it can similarly be challenging to create and maintain a reliable list of clinical concerns or medical problems.

Thus, a longitudinal patient health record contains large amounts of unstructured data, such as physicians' clinical notes from patient encounters, and substantial amounts of structured data such as medications ordered for the patient. However, patient health records generally do not include an accurate list of clinical concerns relevant to the care of a patient. Such a list of clinical concerns, for example, can be used as a part of a clinical summary of the patient's health record. The list of clinical concerns is often called a problems list. Significant medical expertise and a detailed knowledge of the patient record is needed to create and maintain an accurate problem list and, as a result, an accurate problem list for a patient is usually not available.

SUMMARY

Stated broadly methods, systems, and devices herein map data of an electronic medical record to standardized medical concepts using a computerized device. The standardized medical concepts are defined by medical industry standards organizations. The methods, systems, and devices herein identify medical problem concepts, from the standardized medical concepts. These methods, systems, and devices generate feature values of the medical problem concepts based on features within the mapped standardized medical concepts, and weight the medical problem concepts based on the feature values according to a weighting function (using the computerized device). These methods, systems, and devices identify medical problems as ones of the medical problem concepts that have a weighted score above a threshold, according to the weighting, again using the computerized device and output a list of the medical problems from the computerized device.

Other methods, systems, and devices herein map unstructured data of an electronic medical record to first standardized medical concepts, and similarly map unstructured and structured data of the electronic medical record to second standardized medical concepts. The first standardized medical concepts and the second standardized medical concepts are defined by medical industry standards organizations. These methods, systems, and devices herein also identify medical problem concepts using the first standardized medical concepts, and generate features of the electronic medical record using the second standardized medical concepts. With such generated features, these methods, systems, and devices generate feature values of the medical problem concepts. The methods, systems, and devices weight the medical problem concepts based on the feature values according to a weighting function. The methods, systems, and devices identify medical problems as ones of the medical problem concepts that have a weighted score above a threshold, according to the weighting, and output a list of the medical problems from the computerized device.

BRIEF DESCRIPTION OF THE DRAWINGS

The embodiments herein will be better understood from the following detailed description with reference to the drawings, which are not necessarily drawn to scale and in which.

DETAILED DESCRIPTION

As mentioned above, electronic medical patient health records generally do not include an accurate list of clinical concerns (medical problems) relevant to the care of a patient. Further, conventional systems rely upon structured lists or billing classification systems that can only provide incomplete or over inclusive problem lists for the patient's electronic medical record. In view of this, the present methods, devices, and systems identify medical problems from an electronic medical record using natural language processing techniques to generate the pertinent medical problems for a patient.

Figure 1:
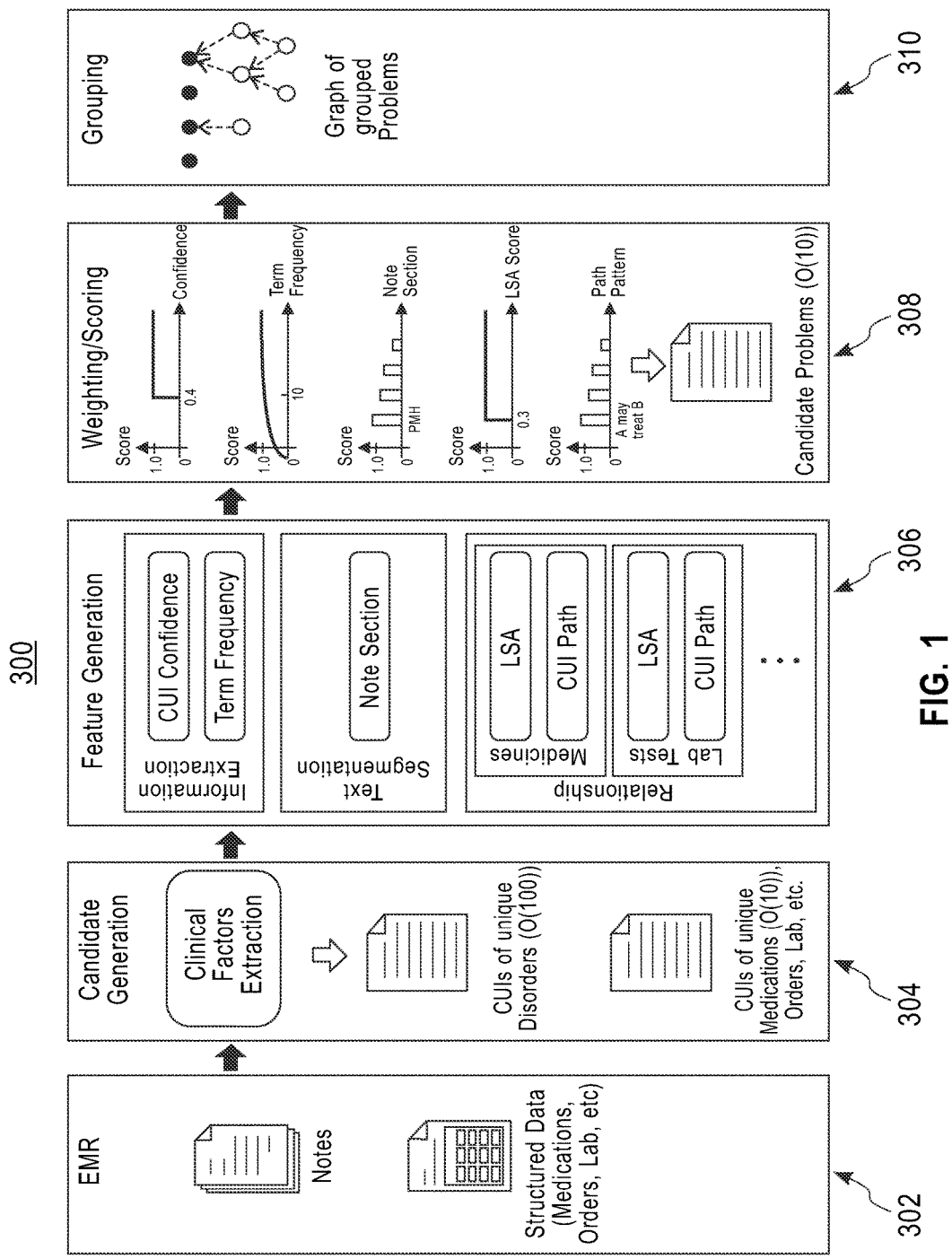
FIG. 1 is a schematic diagram illustrating embodiments herein.

FIG. 1 is a schematic diagram illustrating embodiments of the present methods, devices, and systems. The present methods, devices, and systems provide systems 300 that can identify medical problems from a longitudinal electronic medical record (EMR) 302. The present methods, devices, and systems can use both structured data and unstructured data 302 to perform automated multi-document problem list generation across the entire EMR.

More specifically, a candidate generation module 304 extracts candidate medical concepts from the EMR 302, including both the unstructured and structured data, to map such data to a candidate list of standardized medical concepts from an EMR. In order to perform such mapping, a medical ontology such as the Unified Medical Language System (UMLS) is applied to the structured and unstructured data in the electronic medical record. UMLS contains medical terms having concept unique identifiers (CUIs) relating to medical disorders. The CUI's are standardized terms that provide the agreed or proper semantic terminology to identify a medical problem which otherwise might be identified by many different terms. Thus, once a candidate medical problem is identified from the EMR, it is classified as one of the known CUIs to ensure that the candidate medical problem is identified using the appropriate CUI throughout the processing. For example, the resulting candidate medical problems will includes CUIs of unique disorders, medications, orders, labs, etc.

Such standardized medical concepts are established, defined, cataloged, and maintained within an ontology or dictionary (or similar structured storage) by one or more medical standards organizations. The aforementioned UMLS dictionary CUI's are one example that currently includes over 20,000 standardized CUI's. Another example is a dictionary of standardized medical concepts knows as systematized nomenclature of medical codes (SNOMED codes). For example, the National Library of Medicine (NLM), on behalf of the U.S. Department of Health and Human Services, entered into an agreement with the College of American Pathologists to make SNOMED CT available to U.S. users at no cost through the National Library of Medicine's Unified Medical Language Systems UMLS Metathesaurus. The methods, devices, and systems herein can operate equally well using CUI's, SNOMED codes, or any other dictionary of standardized medical concepts, whether currently known or developed in the future, and CUI's are used herein only as a convenient shorthand for all such repositories.

A feature generation module 306 then processes the candidate medical problems. For each candidate medical problem, features and feature values are generated by applying three techniques including (1) information extraction, (2) text segmentation, and (3) relationship identification. Information extraction includes multiple elements, such as a CUI recognition confidence and a term frequency. Text segmentation involves identification of sections within clinical notes and where the candidate medical problems appear within those sections. The text section feature values may identify a non-numeric feature value such as the name of the section. Relationship identification includes two features; first, latent semantic analysis (LSA) can be used to identify a relationship between a candidate medical problem and medications, lab test results, etc., and second, a CUI path within UMLS may also show relationships between candidate medical problems and medication, lab test results, etc. For every candidate medical problem, the above-mentioned features are generated, and for every feature, a feature score or feature value is generated in item 306.

The feature scores (or feature values) are processed in a scoring/weighting module 308 that generates final scores for each of the candidate medical problems. The scoring/weighting module 308 may use a variety of normalizing functions for each of the feature values. Filtering techniques can be applied. For example, if a score is less than a threshold, the final feature score for the feature is zero; and if the measure is greater than or equal to the threshold then the final feature score is 1.0. Another technique may assign a numerical value to a feature value based on its non-numeric category, for example, for a candidate medical problem appearing in a certain section of an EMR a numerical score may be generated to reflect presence of the problem in that section. For example, different scores can be given based on terms appearing in different locations such as chief complaint, past medical history, social history, family medical history, assessment and plan, etc. Other normalizing functions can be applied as well. Lastly, all of the normalized final scores are combined, and may be weighted according to a weighting function. The weights for the feature values are preferably determined using machine learning. Finally, the candidate medical problems are reduced to a final list of the highest ranking medical problems by applying a threshold, which can also be determined by machine learning.

The feature values described herein are not exclusive, rather additional feature values may be added as new indications of relevance and importance are identified. For example, a feature not shown in FIG. 1 may include a temporal feature to indicate how recent a clinical note was entered from which the candidate medical problem was extracted. The features should therefore be relevant to determining whether a candidate medical problem is a valid medical problem for a patient associated with an EMR. These feature values can be combined using any combination of weighting and scoring functions, and one method of determining the various functions is through the use of machine learning techniques.

The methods herein may also include a grouping module 310 that can automatically group the highest ranking candidate medical problems based on a known medical problem classification hierarchy. Many problems will be closely related or fall under a broader category of problem classification, and the problem list can be further narrowed by grouping such problems together under a broader problem class. More specifically, candidate problems identified as likely problems of a patient in module 308 are grouped in module 310 based on clinical similarities of the problems. For example, Diabetes Mellitus and Diabetes Type II can be grouped into a single problem because one is a specific form of the other. Similarly, Hyperlipidemia and Dyslipidemia can be grouped because they are close variations of each other. Preferably, module 310 uses UMLS provided "isa" relationships and clustering techniques from known art based on characteristics of the problem such as the body part(s) it affects, medications used to treat it, and so on.

Additional aspects of the present methods, devices, and systems include the ability to iteratively improve the problem list by starting the next iteration with the output of the highest ranking standardized medical concepts of the previous iteration as the candidate list of standardized medical concepts (instead of mapping the candidate standardized medical concepts from the electronic medical record). This iteration can continue until no changes or until certain level of problem list scores are obtained.

The present methods, devices, and systems provide a list of a patient's most important medical problems. Having started with the medical concepts identified in clinician's clinical notes 302, the candidate problem list entries are firmly grounded in the patient's condition and experts' observation and judgment. Furthermore, the potential list of standardized medical concepts is not apriori bounded except for the practical limitation of a standard vocabulary, which is usually wide ranging and imposes no limit of practical significance. The scoring processes provide supporting evidence (positively or negatively) in terms of the relevancy of the disorders/diseases to the patient and severity of their clinical concern. Therefore, overall the systems, methods, and devices herein achieve excellent results as measured by recall and precision.

Figure 2:
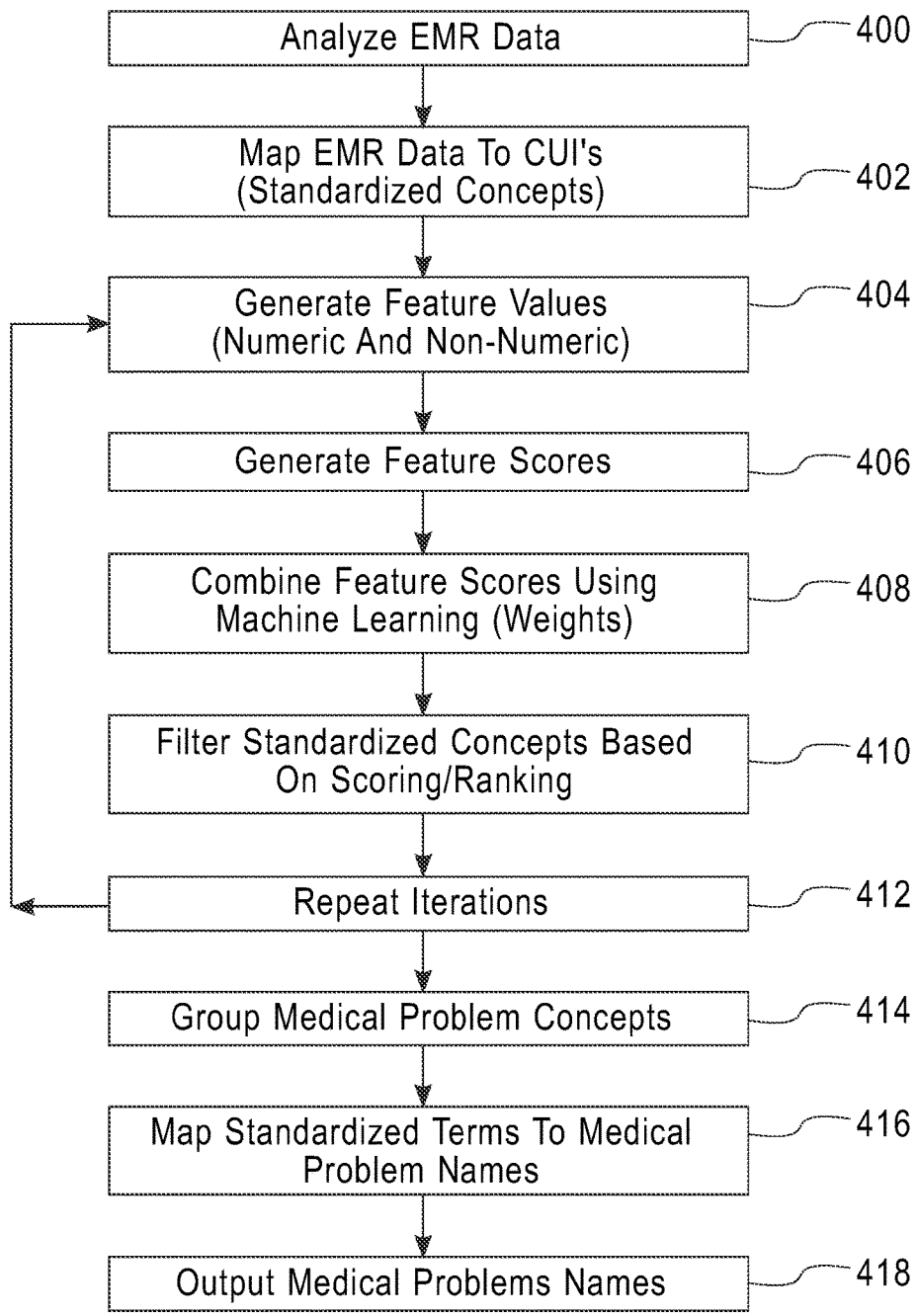
FIG. 2 is a flow diagram illustrating embodiments herein.

FIG. 2 illustrates exemplary methods herein in flowchart form. More specifically, in step 400 the present methods, devices, and systems analyzes data maintained in electronic medical records using a computerized device to identify data items, such as words, prescriptions, test results, etc to generate candidate medical problems. In item 402, these methods map the data to standardized medical concepts, such as CUI's.

The mapping to medical concepts in item 402 may include tokenizing the text, mapping tokens to concepts in a dictionary, and then characterizing further with specific concept types. Thus, the present methods, devices, and systems can map medical terms and other data within the EMR to one or more medical concepts in the UMLS dictionary. The process involves tokenizing text, parsing the text using a language parser, mapping one or more tokens to medical concepts in the UMLS dictionary using matches between the tokens and the dictionary entries (i.e. CUIs in UMLS) along with the text parse and parts of speech taken into account, and then adding additional information so that each recognized concept includes a semantic type (e.g. "finding" or "disease").

Thus, such processes identify terms within the electronic medical records that possibly relate to standardized medical concepts, and also identify what type of medical problem to which these standardized medical concepts are associated. In other words, the processes determine whether a term or other data in the electronic medical record relates to a type of disorder classified by a standardized medical concept (thereby determining that the term or data relates to a candidate medical problem classified by a standardized medical concept) and the processes also identify the specific standardized medical concept to which the term relates. Therefore, such candidate medical problems classified by such standardized medical concepts relate to terms within the electronic medical record that correspond to (generically or specifically) a medical disorder or medical disorder category.

More specifically, the process of analyzing the electronic medical records looks for specific types of medical disorders when mapping to the candidate medical problems classified by standardized medical concepts, and any annotations within the electronic medical records may already indicate the types of disorders that may be associated with each of the candidate medical problems classified by standardized medical concepts.

By identifying specific types of medical disorders, certain types of medical disorders within the electronic medical records can be avoided. For example, it is possible that a medical disorder type of "finding" may be incorrect due to inconsistent wording and it is advantageous to avoid using the findings within the process of identifying candidate medical problems classified by standardized medical concepts because the findings can generate very noisy data.

After mapping to standardized medical concepts in step 402, the methods, systems, and devices herein then generate "feature values" (which can be numeric and non-numeric (e.g., standardized codes, standardized terms, standardized phrases)) of the candidate medical problems from the data within the electronic medical record, in step 404. In step 406, such feature values are scored using multiple scoring processes (depending upon the nature of the feature values). Thus, in item 406 terms may be scored based on frequency or importance values of the terms, test results may be scored differently based on numerical values or percentages relative to acceptable standards, prescription drugs may be scored differently based on quantity, strength, longevity of use, etc. In other words, in item 406, the feature values are classified into different types (or categories), and different scoring processes (or metrics) are applied to each identified feature values depending upon the categorical type that the feature values is classified into, or upon other basis.

In item 408, the feature values (of each feature that relates to a standardized medical concept) are normalized, filtered, and weighted to provide a final combined feature score for each candidate medical problems. The weighting of each feature values can be determined using machine learning techniques. As such, the weighting in step 408 dynamically changes over time as the machine learning processes constantly refine the best weighting parameters to reflect the likelihood that candidate medical problems classified by standardized medical concepts are actual medical problems of patients associated with the electronic medical records. Such machine learning processes can utilize linear regression and classification. For example, the machine learning process may increase the weighting of feature values based on the locations of the medical problem terms within the structure of the electronic medical records, and decrease the weighting of features scores based on how recently the medical problem terms appear within the electronic medical records in response to feedback, and use empirical texting and modeling so as to constantly strive to most accurately match candidate medical problems classified by standardized medical concepts to actual medical problems of patients.

In item 410, the lower scoring/weighted standardized medical concepts are filtered out to allow only the highest-scoring (or highest-ranking) candidate medical problems classified by standardized medical concepts to remain as medical problem concepts. For example, if the final combined feature score for candidate medical problem classified by a standardized medical concept is below a threshold, that candidate medical problem will be removed from the group of probable standardized medical concepts in item 410. The filtering threshold used in item 410 can be manually set or automatically adjusted to increase or decrease the number of medical problem concepts that are output so as to increase/decrease accuracy, change the volume of results output, or achieve other purposes to make the final results output to the user more acceptable.

The initial group of medical problem concepts that are output from item 410 can be reprocessed in multiple iterations using only the highest scoring/weighted medical problem concepts classified by standardized medical concepts produced on a previous iteration, to refine the results as shown by item 412 (and the return arrow to item 404).

The iterations performed in item 412, provide the ability to iteratively improve the problem list by starting the next iteration with the output of the previous iteration as the medical problem concepts (and the methods herein iterate until no changes or until certain level of problem list scores are obtained). More specifically, some of the standardized medical concepts (CUI's) mapped to in item 402 may not have a high relationship to the structured and unstructured data, and such CUI's are referred to as "weak" CUI's. Such weak CUI's can provide potentially erroneous standardized medical concepts and, by repeating the process with only those standardize medical concepts that have a sufficiently high final combined feature score, the additional iterations can remove weak CUI's from the results, increasing the likelihood that the highest ranking standardize medical concepts actually relate to medical problems of the patient.

For example, many unrelated data items in the electronic medical record may map to the same standardize medical concept in item 402, giving such a standardized medical concept an unjustified high feature score; and this high, but in fact "weak," feature score can be removed through the iteration process by repeating the generation (404), scoring (406), weighting (408), and filtering (410) processes using previous results (as opposed to basing the standardized medical concepts only on the actual structured and unstructured data that inappropriately gave an unjustified high feature score on the very first iteration).

In other words, rather than just determining which of the candidate medical problems classified by standardized medical concepts have feature values that have a weighted score above a threshold (item 408), grouping such standardize medical concepts (item 412), mapping the standardized medical concepts back to preferred names (item 414), and outputting the same (item 416) as discussed below; these weak CUI's can be removed by performing multiple iterations where each successive iteration is performed using the highest scoring candidate medical problems classified by standardized medical concepts from the previous iteration.

Following on with processing in FIG. 2, in item 414 the highest scoring/weighted medical problem concepts are grouped (as discussed above with respect to item 310). Thus, in step 414, the medical problem concepts are grouped using a medical problem classification hierarchy (e.g., related disorders, disorder classifications, etc.) and may be consolidated into a smaller list based on the relations and classes of medical problems.

In item 416, the most probable standardize medical concepts (that result from initial or iterative processing) represented as medical problem concepts here, are mapped back from the standardized medical concepts (e.g., codes) to a more user-friendly words, such as natural language "preferred names" to be more easily understood by the user. Thus, in item 416, these methods map the standardized medical concepts that are ranked highly enough to preferred names (preferred names) that are natural language descriptions of the standardized medical concepts.

In item 418, these preferred names output in a ranked order according to weighted feature values of the features of the standardized medical concepts (e.g., a ranked order using the final combined feature score of each standardized medical concept, with higher-ranked items being presented before lower-ranked items).

Thus, these methods map data of an electronic medical record to standardized medical concepts, rank and filter the standardized medical concepts, and then map back out to natural language preferred names. These methods generate feature values of the standardized medical concepts by applying different scoring processes to feature values within the data of the electronic medical record using the computerized device. The different scoring processes score the feature values differently by applying different weighting/scoring metrics to the data of the electronic medical record. These methods identify medical problem concepts as ones of the standardized medical concepts that have a combined feature score above a threshold. Thus, these methods can map the medical problem concepts back to preferred names and output a list of the preferred names from the computerized device in ranked order.

The present methods, devices, and systems may apply thresholds to each of the scores to reduce the number of feature values that need to be weighted to filter the feature values. Alternatively, the filtering can be performed in the subsequent weighting process. The choice of when to conduct such filtering depends upon the number of feature values that need to be analyzed verses the need for accuracy. Understandably, if more feature values are filtered out early in the process, the thoroughness of the process decreases. However, if filtering of feature values is performed later in the process, the process is more resource intensive, making the process run slower on computerized systems, more computationally expensive, etc.

Figure 3:
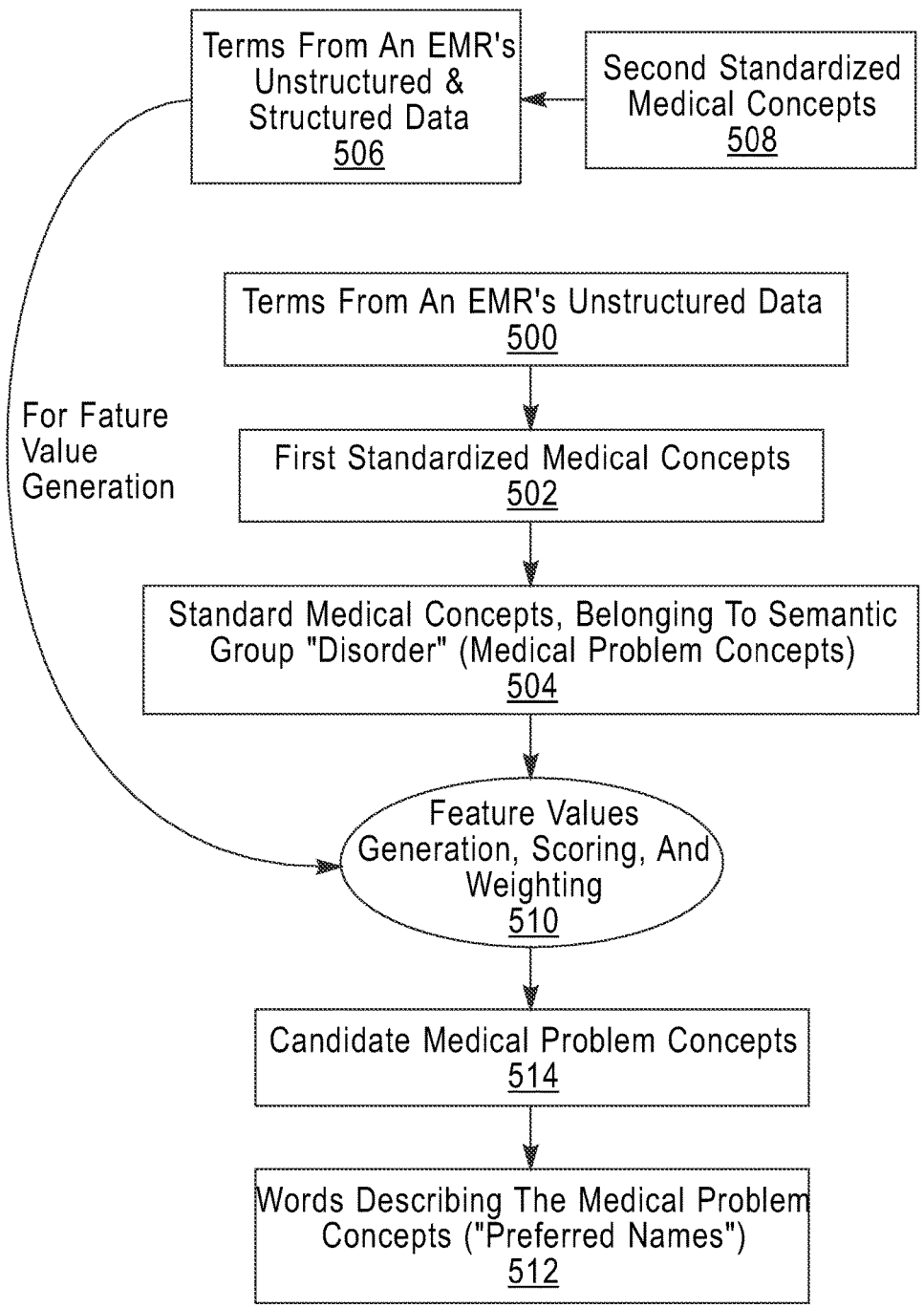
FIG. 3 is a flow diagram illustrating embodiments herein.

Therefore, as shown in FIG. 3, methods, systems, and devices herein map unstructured data of an electronic medical record 500 to first standardized medical concepts 502, and similarly map structured and unstructured data of an electronic medical record 506 to second standardized medical concepts 508 using a computerized device. The standardized medical concepts 502, 508 are defined by medical industry standards organizations and can comprise numerical codes representing disorders, standardized terms representing disorders, etc. (such as CUI's, SNOMED codes, etc.).

In item 504, the methods, systems, and devices herein identify medical concepts of type disorder (as defined by the standard organizations) as medical problem concepts, from the first standardized medical concepts 502 that are based on unstructured data. In item 510, these methods generate feature values of the medical problem concepts by scoring such features within the second standardized medical concepts 508 that are based on the structured and unstructured data of the electronic medical record. Further, in item 510, these methods weight the medical problem concepts based on the feature values according to a weighting function (using the computerized device). In item 514, these methods, systems, and devices identify medical problem concepts as ones of the medical problem concepts that have a weighted score above a threshold, according to the weighting, again using the computerized device. The methods, systems, and devices herein then map the medical problem concepts to preferred names and output a list of the preferred names from the computerized device in item 514.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

In the on-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for loadbalancing between clouds).

A cloud computing environment is service oriented with a focus on statelessness, low coupling, modularity, and semantic interoperability. At the heart of cloud computing is an infrastructure comprising a network of interconnected nodes.

Figure 4:
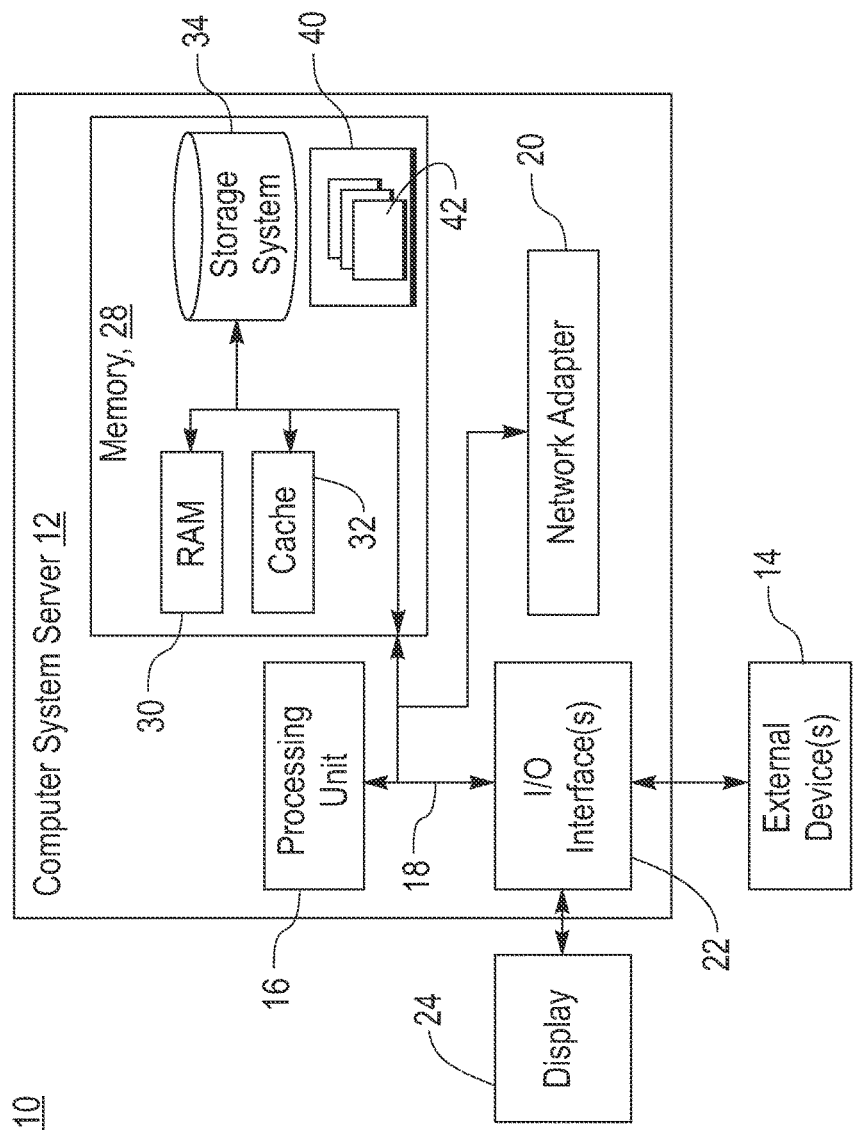
FIG. 4 is a schematic diagram of a hardware system used by systems and methods herein.

Referring now to FIG. 4, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 5:
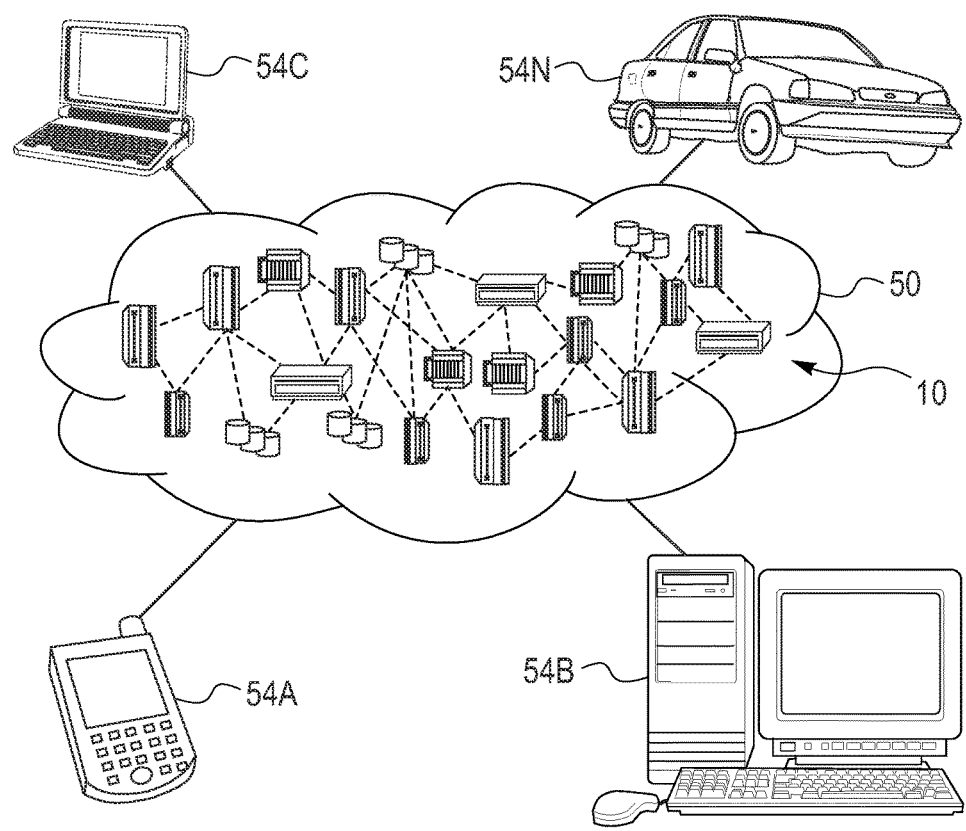
FIG. 5 is a schematic diagram of a computing environment according to embodiments herein.

Referring now to FIG. 5, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 5 are intended to be illustrative only and that computing nodes 10 and cloud computing environment 50 can communicate with any type of computerized device over any type of network and/or network addressable connection (e.g., using a web browser).

Figure 6:
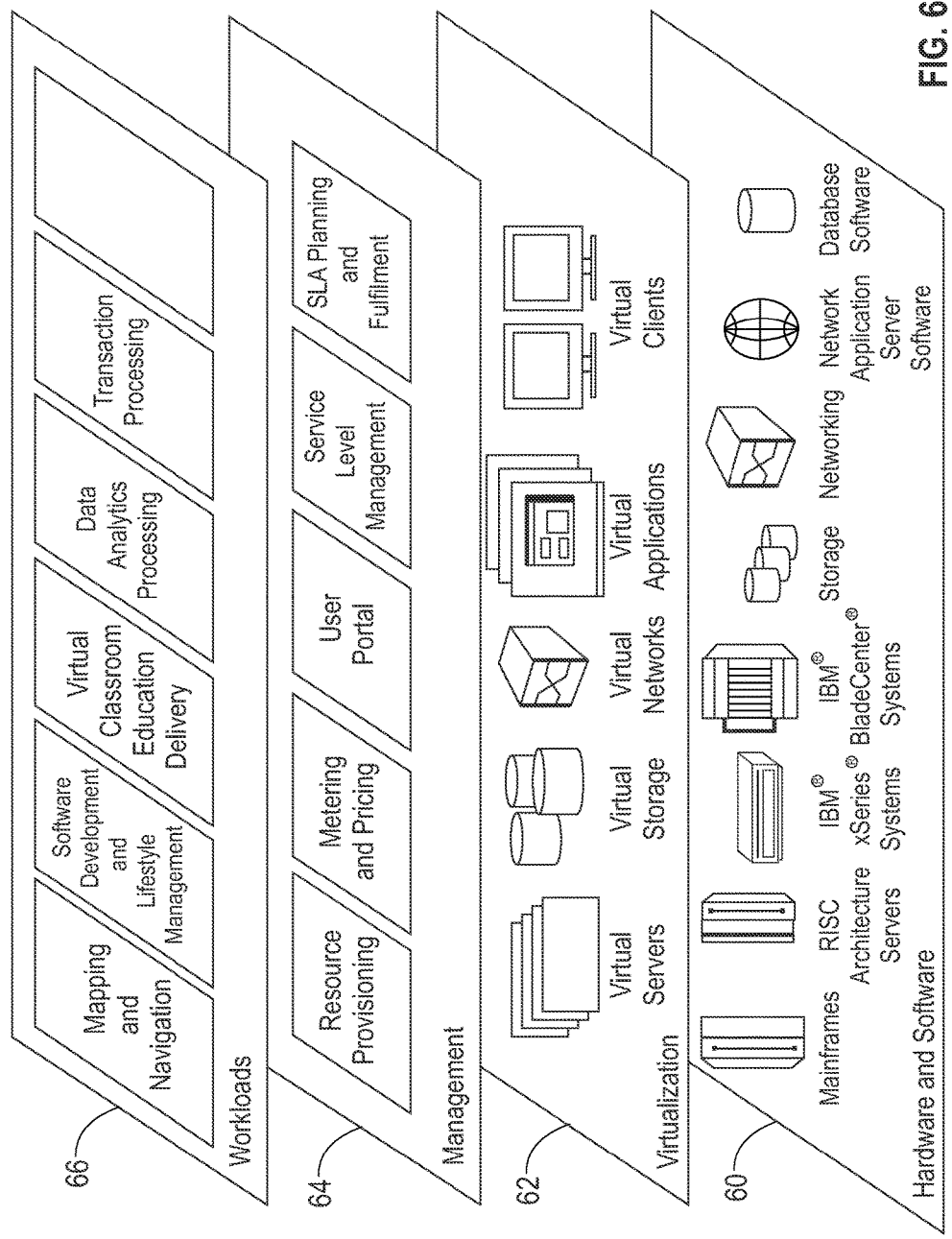
FIG. 6 is a schematic diagram of a functional abstract layers according to embodiments herein.

Referring now to FIG. 6, a set of functional abstraction layers provided by cloud computing environment 50 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing, and automated problem list generation from an EMR according to the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments.

The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer implemented method comprising:
    mapping data from an electronic medical record maintained in computerized systems to standardized medical concepts in an ontology to identify candidate medical problems of a patient associated with said electronic medical record;
    generating and scoring feature values for said candidate medical problems by scoring said feature values based on identification of sections of said electronic medical record where said candidate medical problems appear to assign a numerical value to a feature value based on a non-numeric category within said electronic medical record, scoring said feature values based on how recent a clinical note was entered from which a candidate medical problem was extracted, and scoring said feature values based on strength of relationships between: said standardized medical concepts and prescribed medications identified within said electronic medical record; and said standardized medical concepts and laboratory test results within said electronic medical record;
    weighting said feature values according to a weighting function that determines how likely said candidate medical problems are actual medical problems of said patient associated with said electronic medical record to generate a weighted score for said feature values of said candidate medical problems of said patient;
    filtering said candidate medical problems that have said feature values with said weighted score below a threshold to leave medical problem concepts of said patient; and
    outputting a list of said medical problem concepts from a computerized device.

2. The method according to claim 1, further comprising automatically performing at least one additional iteration of said weighting using only said candidate medical problems produced on a previous iteration.

3. The method according to claim 1, said generating and scoring feature values comprising evaluating locations of said electronic medical record, said locations comprising physician clinical notes, nurse practitioner clinical notes, discharge notes, outpatient notes, testing technician notes, past medical history, social history, and family medical history.

4. The method according to claim 1, said weighting uses machine learning processes utilizing at least one of linear regression and classification.

5. The method according to claim 1, further comprising setting a weighting threshold for said weighting using machine learning processes, said machine learning processes utilizing at least one of linear regression and classification.

6. The method according to claim 1, said mapping identifying said standardized medical concepts using processes comprising rules identifying specific types of known medical disorders.

7. A method comprising:
mapping unstructured data of an electronic medical record maintained in computerized systems to first standardized medical concepts in an ontology and mapping unstructured and structured data of said electronic medical record to second standardized medical concepts in said ontology to identify candidate medical problems of a patient associated with said electronic medical record;
identifying medical problem concepts using said first standardized medical concepts;
generating and scoring feature values for said candidate medical problems by scoring said feature values based on identification of sections of said electronic medical record where said candidate medical problems appear to assign a numerical value to a feature value based on a non-numeric category within said electronic medical record, scoring said feature values based on how recent a clinical note was entered from which a candidate medical problem was extracted, and scoring said feature values based on strength of relationships between: said second standardized medical concepts and prescribed medications identified within said electronic medical record; and said second standardized medical concepts and laboratory test results within said electronic medical record;
dynamically weighting said feature values according to a weighting function that determines how likely said candidate medical problems are actual medical problems of said patient associated with said electronic medical record to generate a weighted score for said feature values of said candidate medical problems of said patient;
filtering said candidate medical problems that have said feature values with said weighted score below a threshold to leave medical problem concepts of said patient; and
outputting a list of said medical problem concepts from a computerized device.

8. The method according to claim 7, further comprising automatically performing at least one additional iteration of said weighting using only said candidate medical problems produced on a previous iteration.

9. The method according to claim 7, said generating and scoring feature values comprising evaluating locations of said electronic medical record, said locations comprising physician clinical notes, nurse practitioner clinical notes, discharge notes, outpatient notes, testing technician notes, past medical history, social history, and family medical history.

10. The method according to claim 7, said weighting uses machine learning processes utilizing at least one of linear regression and classification.

11. The method according to claim 7, further comprising setting a weighting threshold for said weighting using machine learning processes, said machine learning processes utilizing at least one of linear regression and classification.

12. The method according to claim 7, said mapping identifying said first standardized medical concepts and said second standardized medical concepts using processes comprising rules identifying specific types of known medical disorders.

13. A computer program product, said computer program product comprising a computer readable storage medium having program instructions embodied therewith, wherein the computer readable storage medium is not a transitory signal per se, the program instructions being executable by a computer, to perform a method comprising:
automatically, by said computer, mapping data from an electronic medical record maintained in computerized systems to standardized medical concepts in an ontology to identify candidate medical problems of a patient associated with said electronic medical record;
automatically, by said computer, generating and scoring feature values for said candidate medical problems by scoring said feature values based on identification of sections of said electronic medical record where said candidate medical problems appear to assign a numerical value to a feature value based on a non-numeric category within said electronic medical record, scoring said feature values based on how recent a clinical note was entered from which a candidate medical problem was extracted, and scoring said feature values based on strength of relationships between: said standardized medical concepts and prescribed medications identified within said electronic medical record; and said standardized medical concepts and laboratory test results within said electronic medical record;
automatically, by said computer, dynamically weighting said feature values according to a weighting function that determines how likely said candidate medical problems are actual medical problems of said patient associated with said electronic medical record to generate a weighted score for said feature values of said candidate medical problems of said patient;
automatically, by said computer, filtering said candidate medical problems that have said feature values with said weighted score below a threshold to leave medical problem concepts of said patient; and
automatically, by said computer, outputting a list of said medical problem concepts.

14. The computer program product according to claim 13, further comprising automatically performing at least one additional iteration of said weighting using only said candidate medical problems produced on a previous iteration.

15. The computer program product according to claim 13, said generating and scoring feature values comprising evaluating locations of said electronic medical record, said locations comprising physician clinical notes, nurse practitioner clinical notes, discharge notes, outpatient notes, testing technician notes, past medical history, social history, and family medical history.

16. The computer program product according to claim 13, said weighting uses machine learning processes utilizing at least one of linear regression and classification.

17. The computer program product according to claim 13, further comprising setting a weighting threshold for said weighting using machine learning processes, said machine learning processes utilizing at least one of linear regression and classification.

* * * * *